United States Patent [19]

Parlman

[11] 4,299,996
[45] Nov. 10, 1981

[54] ALKYL ARYL ETHER PRODUCTION

[75] Inventor: Robert M. Parlman, Bartlesville, Okla.

[73] Assignee: Phillips Petroleum Co., Bartlesville, Okla.

[21] Appl. No.: 132,600

[22] Filed: Mar. 21, 1980

[51] Int. Cl.$^3$ ............................................. C07C 41/06
[52] U.S. Cl. .................................. 568/658; 568/631; 568/632
[58] Field of Search ................ 568/632, 697, 658, 631

[56] References Cited

U.S. PATENT DOCUMENTS

| | | | |
|---|---|---|---|
| 2,477,091 | 7/1949 | Rosenwald | 568/658 X |
| 2,655,546 | 10/1953 | Stevens et al. | 568/658 X |
| 3,282,875 | 11/1966 | Connolly et al. | 260/29.6 F |
| 4,153,810 | 5/1979 | Neumann et al. | 568/632 X |

*Primary Examiner*—Bernard Helfin

[57] ABSTRACT

Phenol compounds are O-alkylated with olefins in the presence of acid resin catalysts to give aryl alkyl ethers. In a preferred embodiment, the catalyst comprises perfluorosulfonic acid ion exchange resins.

7 Claims, No Drawings

ALKYL ARYL ETHER PRODUCTION

THE INVENTION

This invention relates to a process for preparing ethers. In another aspect, this invention relates to the preparation of ethers by contacting a phenol with an olefin in the presence of a catalyst system. In a further aspect, this invention relates to the preparation of alkyl aryl ethers using an acid ion exchange resin catalyst. In another aspect, this invention relates to the preparation of alkyl aryl ethers from a phenol and an olefin in the presence of a perfluorosulfonic acid ion exchange resin to produce a product comprising O-alkylated materials.

BACKGROUND OF THE INVENTION

Alkyl aryl ethers are excellent solvents for organic residues and are particularly good for dissolving the resinous or varnish-like deposits formed in the crankcase of internal combustion engines. They are also used as antioxidants, heat-transfer agents, and ingredients in perfumes. So far as can be determined, no efficient and economical method is known whereby alkyl aryl ethers can be prepared in desirable quantities. The Williamson synthesis appears to be the most important method involving the reaction between an alkali metal salt of a hydroxy aromatic compound like phenol or cresol and an alkyl halide or sulfate ester. The yields are generally low and there is a disposal problem with the alkali metal salt by-products. Phenols are reported in British Pat. No. 600,837 (Chem. Abst. 42:7334e) to be alkylated with an alcohol using an alumina or silica catalyst to give mixtures of alkylated phenols and phenolic ethers, the latter being produced in about 43 wt. % yield by recycling unreacted phenol. U.S. Pat. No. 2,655,546 discloses the synthesis of alkyl aryl ethers at 65° C. from phenol and olefins using acid catalysts such as sulfuric acid, chlorosulfonic acid, benzenesulfonic acid, alkyl acid sulfates and the like. The disadvantage of this and other such methods involving acid catalysts is that product separation and purification involves aqueous alkali metal hydroxide washes to neutralize and remove the catalyst. The current invention attempts to overcome some of the heretofore mentioned difficulties by providing a synthesis method for the preparation in high selectivity of alkyl aryl ethers from phenols and olefins at ambient conditions employing a heterogeneous catalyst such that a subsequent neutralization step with alkali metal hydroxides is unnecessary.

Accordingly, it is an object of this invention to provide a novel process for the preparation of ethers.

Another object of this invention is to provide a process for the preparation of ethers wherein the product comprises O-alkylated materials.

Other objects, aspects, as well as the several advantages of the invention will be readily apparent to those skilled in the art upon reading the specification and appended claims.

SUMMARY OF THE INVENTION

In accordance with the invention, alkyl aryl ethers are produced by reacting a phenol and an olefin in the presence of an acid ion exchange resin catalyst under conditions which form a product containing O-alkylated materials.

In accordance with one specific embodiment, hydroxy aromatic compounds are O-alkylated with olefins in the presence of a perfluorosulfonic acid ion exchange resin catalyst to give aryl alkyl ethers.

In another specific embodiment, a mixed cresol stream is contacted with isobutylene in the presence of a perfluorosulfonic acid resin catalyst under conditions which give a relatively high percentage of O-alkylated products rather than C-alkylated products.

DETAILED DESCRIPTION OF THE INVENTION

A. Hydroxy Aromatic Compounds

The present invention is applicable to the reaction of phenols broadly including mononuclear phenols as well as condensed polynuclear phenols, such as naphthols. Exemplary of the phenols which are employed in preparing ethers by the process of the present invention are hydroxy aromatic compounds represented by the formulas

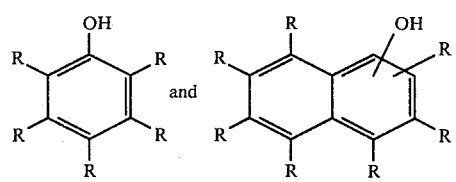

wherein each R can be hydrogen or any alkyl or cycloalkyl radical having from 1 to 6 carbon atoms. For example, materials to be used that correspond to the above formulas are, but not limited to phenol, o-cresol, m-cresol, p-cresol, 2,3-xylenol, 2,4-xylenol, 2,5-xylenol, 2,6-xylenol, 3,4-xylenol, 3,5-xylenol, 2,3,4-trimethylphenol, 2,3,5-trimethylphenol, 2,3,6-trimethylphenol, 2,4,6-trimethylphenol, 3,4,5-trimethylphenol, 2-ethylphenol, 2-hexylphenol, 2,4-dihexylphenol, 2-methyl-4-ethylphenol, 2-cyclohexylphenol, α-naphtol, β-naphthol, and the like, and mixtures thereof.

B. Olefins

Olefins useful in this invention are those materials represented by the formula

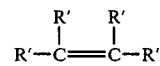

wherein R′ can be hydrogen or any alkyl, cycloalkyl or aryl radical having from 1 to 16 carbon atoms and wherein the total number of carbon atoms does not exceed 18. Materials to be used in this invention that correspond to the above olefin formula are, but not limited to, for example, ethylene, propylene, 1-butene, 2-butene, 2-methyl-1-propene (isobutylene), 1-pentene (n-amylene), 2-methyl-1-butene (iso-amylene), 3-methyl-1-butene, 2-pentene, 2-methyl-2butene, 1hexene, 3,3,-dimethyl-1butene, 2,3-dimethyl-2-butene, 2-methyl-2-pentene, 1-octene, 2-octene, 2,4,4-trimethyl-2-pentene, 1-decene, 1-dodecene, 1-tetradecene, 1-hexadecene, vinylcyclohexane, styrene, and the like, and mixtures thereof.

Generally, the olefin to phenol mole ratio will be at least 1:1, preferably 1.1–3.0:1. Because of the higher volatility of the olefin and its subsequent ease of separation when unreacted, it is preferred to employ an excess of olefin.

In forming alkyl aryl ethers, in accordance with this invention, a suitable phenol and olefin are contacted under conditions which produce a product containing a relatively high percentage of O-alkylated materials. For example, a mixed cresol stream comprising 65% m-cresol, 32% p-cresol, and 4% xylenols when treated with isobutylene in the presence of perfluorosulfonic acid resin catalyst yields a product containing 45-65 wt. % of m/p-cresol-t-butyl ether.

C. Catalyst

The catalysts useful in this invention are perfluorosulfonic acid ion exchange resins. The particular catalyst used in the specific examples of this invention was Nafion ® 511 (Equivalent weight, 1100) produced by E. I. DuPont. Nafion products are copolymers of tetrafluoroethylene and monomers such as perfluoro-3,6-dioxa-4-methyl-7-octensulfonic acid and are represented by the general formula

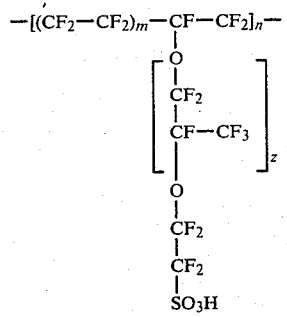

in which m can be as low as 5 and as high as 13.5, n can be about 1,000 and z equals 1,2,3 ... The lower value of m corresponds to an equivalent weight of 950 and the higher value to 1800. On this basis, the particular catalyst employed herein, Nafion ® 511 (equivalent weight equal to 1100) would have an m value estimated to be 6.5. In terms of ion exchange capacity, the range is from 1.05 meq./g to 0.55 meq/g. Generally, the catalyst must initially be in the free acid form to be effective. For this reason, catalyst available as a salt (e.g., potassium) can be mildly pretreated with a dilute mineral acid such as 15 wt. % aqueous nitric acid, water washed and dried before using.

The amount of catalyst employed can be broadly 0.5 to 20 g/mole of hydroxy aromatic compound, preferably 1 to 10 g/mole of hydroxy aromatic compound. In terms of ion exchange capacity, this is equivalent to broadly 0.275 to about 21 meq./g, preferably 0.55 to about 10 meq/g. In the invention runs of Example III, the amount of catalyst employed was 8 g/mole of hydroxy aromatic compound (cresol).

D. Solvents

Solvents are not required in the current invention. Nevertheless, if solvents are used they can be present from about 10 to 50 wt. % and must be inert. For example, saturated hydrocarbon solvents such as pentane, hexane, octane, petroleum ether can be employed.

E. Reaction Conditions

The reaction conditions can vary appreciably depending upon the particular reactants employed but will be sufficient to produce a product containing O-alkylated materials. The reaction can be conducted over a broad temperature and pressure range as shown

| Temperature, °C. | −25 to 150 |
|---|---|
| Pressure, psig | 0 to 1000 |

The reaction can be carried out in any suitable equipment and manner, such as batch or continuous operation. The reaction of the olefin with the phenol involves no special difficulties with the reacting ingredients being simply contacted in any suitable manner. The catalyst is often first mixed with a phenol and the olefin is then, with agitation, if necessary, passed into the mixture thus formed. When the olefin is a gas under the existing reaction conditions, it is ordinarily passed through the mixture and absorbed until the predetermined gain in weight is obtained or until rate of gain in weight becomes impractically slow. The reaction can be carried out under elevated pressures or reduced pressures as well as at atmospheric pressure.

A variety of conventional methods including distillation, extraction, phase separation, etc., can be utilized to recover the reaction product, unreacted starting materials, catalysts, and diluent, if used.

The following examples serve to illustrate the operability of this invention.

EXAMPLE I

This example describes the general experimental procedure used herein to react aromatic hydroxy compounds and olefins. In addition, this example is a control run illustrating the preparation of C-alkylated products from phenols and olefins in the presence of a heterogeneous sulfonic acid resin catalyst.

Into a 6 ounce Fisher-Porter bottle containing a stirring bar, was added 2 grams of Amberlyst ® 15, a polystyrene-based heterogeneous sulfonic acid exchange resin catalyst supplied by Rohm and Haas Company, followed by 27 grams (0.25 mole) of a cresol mixture comprised of 64 wt. % m-cresol, 33 wt. % p-cresol, and 3 wt. % xylenol. The bottle was sealed with the Fisher head equipped with a pressure gauge and two hole valves with female Swagelok ® fittings. This bottle was then connected via a flexible tube to another Fisher-Porter bottle containing 42 grams (0.75 mole) of isobutylene. The olefin containing bottle was inverted and the isobutylene allowed to flow freely into the reaction vessel which was previously positioned in a warm water bath at 50° C. After 1 hour at 50° C. with stirring, the contents and bottle were quickly cooled to about 25° C. and the excess isobutylene vented. The remainder of the liquid in the bottle was analyzed by chromatography. The results showed 100% conversion of the cresols to C-alkylated products. The product distribution was 38 wt. % monobutylated cresols and 62 wt. % dibutylated cresols. Analysis was carried out by a known silylation technique whereby ortho and meta isomers are easily identified. This analysis was as follows: into a 5 milliliter vial was placed 2 milliliters of Regisil ® silylating agent, N,O-bis(trimethylsilyl)trifluoroacetamide from Regis Chemical Co., and 0.5 milliliters of the butylated cresol reaction mixture. This reagent reacts with the hydroxyl group of the cresol forming a trimethylsiloxy group which aids in the separation of the cresol isomers. The analysis mixture was then subjected to GLC analysis using a 10 ft.×⅛ in. stainless steel column packed with 10 wt. % Carbowax 20 M on Chromosorb P(NAW), 80–100 mesh.

EXAMPLE II

This example is another control using conventional alkylation catalysts. The procedure described in Example I was repeated except 0.5 gram of concentrated $H_2SO_4$ was employed as a catalyst instead of Amberlyst 15. Analysis indicated only C-alkylated products are formed. The results showed a 98.5 wt. % cresol conversion at 25° C. giving an analysis distribution of 92.5 wt. % dibutylated cresols, 7 wt. % monobutylated cresols, and 1.5 wt. % unreacted cresols. When the reaction was conducted at 0° C., analysis of the reaction mixture showed 3.1 wt. % unreacted cresols, 17.8 wt. % monobutylated cresols, and 61.0 wt. % cresols.

Conducting the alkylation in the presence of other alkylation catalysts such as 2 grams $H_3PO_4$/Kieselguhr or 2 grams $H_2SO_4$/Millwhite at 0° C., 25° C., or 50° C. gave 100 wt. % unreacted cresols.

EXAMPLE III

This example is an inventive run illustrating that when aromatic hydroxy compounds and olefins are reacted in the presence of a heterogeneous perfluorosulfonic acid exchange resin catalyst the major products are ethers (O-alkylated products). The procedure described in Example I was repeated except 2 grams of Nafion ® 511 (from E. I. DuPont) was used as the catalyst instead of Amberlyst 15. Nafion 511 is commercially available as the potassium salt and was converted to the free acid before using as a catalyst by pre-treating the resin with 15 wt. % aqueous $HNO_3$, water washing and drying. When the reaction was conducted at 50° C., GLC-Mass Spectrometer analysis showed 34.1 wt. % unreacted cresols, 6.5 wt. % monobutylated cresols, 11.5 wt. % dibutylated cresols and 45 wt. % butylated ethers (O-alkylated m,p-ethers). Conducting the reaction at lower temperatures gave slightly better cresol conversions and higher amounts of ethers. For example, when the reaction was conducted at 25° C., GLC-Mass analysis showed the resulting reaction mixture to contain 32.9 wt. % unreacted cresols, 1 wt. % monobutylated cresols, 2 wt. % dibutylated cresols and 56 wt. % butylated ethers. Conducting the reaction at 0° C. gave almost the same results as at 25° C.

SUMMARY

The results herein disclosed are summarized in Table I wherein it is shown the inventive process involving heterogeneous perfluorosulfonic acid exchange resins as catalysts permit the formation of O-alkylated products (ethers) while other alkylation catalyst such as $H_2SO_4$ and other non-fluorinated sulfonic acid exchange resins give only C-alkylated products and no O-alkylated products.

I claim:

1. An O-alkylation process for the production of alkyl aryl ethers which comprises reacting a phenol and an olefin in the presence of a perfluorosulfonic acid ion exchange resin catalyst under alkylation conditions which produce a product containing a high percentage of O-alkylated products rather than C-alkylated products.

2. A process according to claim 1 wherein said phenol is a hydroxy monocyclic aromatic compound represented by the formulas

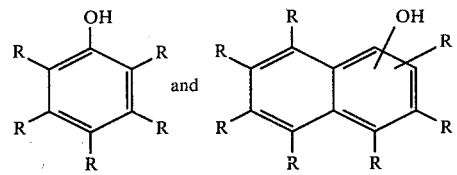

wherein each R can be hydrogen or any alkyl or cycloalkyl radical having from 1 to 6 carbon atoms and said olefin is represented by the formula

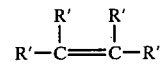

wherein R′ can be hydrogen or any alkyl, cycloalkyl or aryl radical having from 1 to 16 carbon atoms and wherein the total number of carbon atoms does not exceed 18.

3. A process according to claim 1 wherein said phenol is a mixture of cresols.

4. A process according to claim 1 wherein the olefin to phenol mole ratio is at least 1:1 and the temperature

TABLE I

Effect of Catalyst on Alkylation Product Distribution
From the Reaction of Cresol and Isobutylene

| Example No. | Catalyst, grams | Reaction Temp., °C. | Wt. % by GLC | | | |
|---|---|---|---|---|---|---|
| | | | Unreacted m,p-Cresols[a] | C-Alkylated Products[a] | | O-Alkylated Products |
| | | | | Mono-Subst. | Di-Subst. | m,p-Ethers |
| I | Sulfonic Acid Exchange Resin[c], 2 grams | 50 | — | 38 | 62 | — |
| II-A | Conc. $H_2SO_4$, 0.5 grams | 0 | 3.1 | 17.8 | 61.0 | — |
| | | 25 | 1.5 | 7 | 92.5 | — |
| II-B | $H_3PO_4$/Kieselguhr, 2 grams | 0 | 100 | — | — | — |
| | | 25 | 100 | — | — | — |
| | | 50 | 100 | — | — | — |
| II-C | $H_2SO_4$/Millwhite, 2 grams | 0 | 100 | — | — | — |
| | | 25 | 100 | — | — | — |
| | | 50 | 100 | — | — | — |
| III | Perfluorosulfonic Acid Exchange Resin[d], 2 grams | 0[e] | 32.9 | 1 | 1 | 56 |
| | | 25[e] | 32.9 | 1 | 2 | 56 |
| | | 50 | 34.1 | 6.5 | 11.5 | 45 |

[a]GLC analysis by Regisil technique.
[b]Ethers determined by GLC-Mass Spectrometer.
[c]Amberlyst 15, Rohm and Haas Company.
[d]Nafion 511 converted to H+ form by pre-treating with 15 wt. % $HNO_3$.
[e]GLC results are based on the average of 2 determinations.

is in the range of about −25° C. to about 150° C. and the pressure ranges from about 0 to about 1000 psig.

5. A process according to claim 1 wherein the phenol comprises cresol and the olefin is isobutylene.

6. A process according to claim 1 wherein the amount of said catalyst employed ranges from 0.5 to 20 g/mole of phenol.

7. A process according to claim 1 for producing O-alkylated products comprising m,p-ethers comprising reacting a mixture of cresols with isobutylene in the presence of a heterogeneous perfluorosulfonic acid exchange resin catalyst at ambient conditions.

* * * * *